United States Patent [19]

Fontaine

[11] Patent Number: 5,314,472
[45] Date of Patent: May 24, 1994

[54] VASCULAR STENT

[75] Inventor: Arthur B. Fontaine, Fresno, Calif.

[73] Assignee: Cook Incorporated, Bloomington, Ind.

[21] Appl. No.: 769,216

[22] Filed: Oct. 1, 1991

[51] Int. Cl.$^5$ .................. A61F 2/04; A61F 2/06; A61M 29/02
[52] U.S. Cl. ............................ 623/12; 623/1; 606/194; 606/195
[58] Field of Search ............... 623/1, 11, 12; 606/192, 606/193, 194, 195

[56] References Cited

U.S. PATENT DOCUMENTS

| | | | |
|---|---|---|---|
| 4,512,338 | 4/1985 | Balko et al. | 128/1 R |
| 4,553,545 | 11/1985 | Maass et al. | 606/198 |
| 4,580,568 | 4/1986 | Gianturco | 128/345 |
| 4,649,922 | 3/1987 | Wiktor | 128/344 |
| 4,655,771 | 4/1987 | Wallsten | 623/1 |
| 4,665,918 | 5/1987 | Garza et al. | 128/343 |
| 4,732,152 | 3/1988 | Wallsten et al. | 623/1 |
| 4,733,665 | 3/1988 | Palmaz | 623/1 |
| 4,739,762 | 4/1988 | Palmaz | 623/1 |
| 4,776,337 | 10/1988 | Palmaz | 623/1 |
| 4,787,899 | 11/1988 | Lazarus | 623/1 |
| 4,795,458 | 1/1989 | Regan | 623/1 |
| 4,800,882 | 1/1989 | Gianturco | 606/194 |
| 4,820,298 | 4/1989 | Leveen et al. | 623/1 |
| 4,830,003 | 5/1989 | Wolff et al. | 623/1 |
| 4,848,343 | 7/1989 | Wallsten et al. | 604/271 |
| 4,856,516 | 8/1989 | Hillstead . | |
| 4,875,480 | 10/1989 | Imbert . | |
| 4,878,906 | 11/1989 | Lindemann et al. . | |
| 4,881,547 | 11/1989 | Danforth . | |
| 4,886,062 | 12/1989 | Wiktor . | |
| 4,893,623 | 1/1990 | Rosenbluth . | |
| 4,922,905 | 5/1990 | Strecker . | |
| 4,950,227 | 8/1990 | Savin et al. . | |
| 4,954,126 | 9/1990 | Wallsten . | |
| 4,969,458 | 11/1990 | Wiktor | 606/194 |
| 4,969,890 | 11/1990 | Sugita et al. . | |
| 5,015,253 | 5/1991 | MacGregor | 623/1 |
| 5,019,090 | 5/1991 | Pinchuk | 606/194 |
| 5,035,706 | 7/1991 | Gianturco | 606/198 |
| 5,041,126 | 8/1991 | Gianturco | 606/195 |
| 5,133,732 | 7/1992 | Wiktor | 606/195 |
| 5,135,536 | 8/1992 | Hillstead | 606/195 |
| 5,183,085 | 2/1993 | Timmermans | 623/1 |
| 5,197,978 | 3/1993 | Hess | 623/1 |

FOREIGN PATENT DOCUMENTS

| | | | |
|---|---|---|---|
| 183372 | of 1986 | European Pat. Off. | A61M 29/00 |
| 2811372 | 11/1978 | Fed. Rep. of Germany | 623/12 |

*Primary Examiner*—David Isabella
*Assistant Examiner*—Debra S. Brittingham
*Attorney, Agent, or Firm*—Richard J. Godlewski

[57] ABSTRACT

A vascular stent includes at least one filament formed into a wave-like pattern, the filament being wound into a substantially spiral shape; and a device for connecting at least one end of the filament to slide on a another portion of the filament so as to form a hoop at each end of the spiral shape.

20 Claims, 4 Drawing Sheets

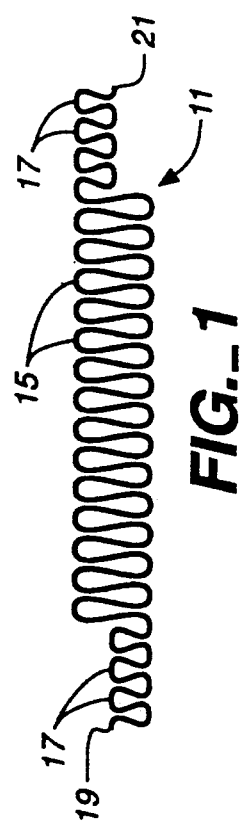
FIG._1
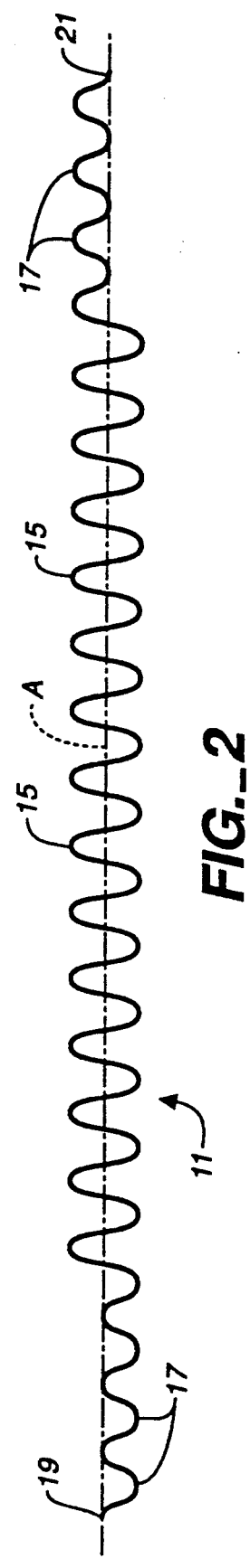
FIG._2
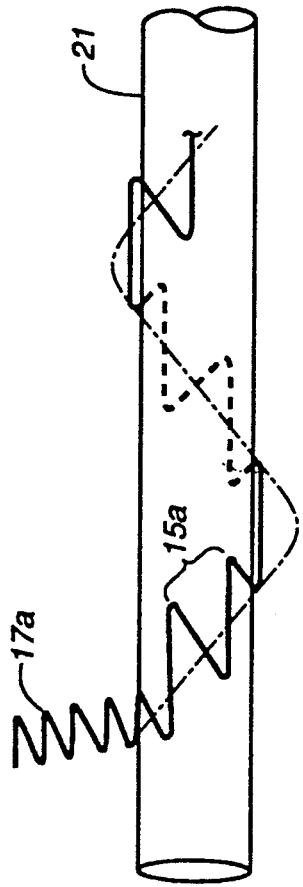
FIG._5
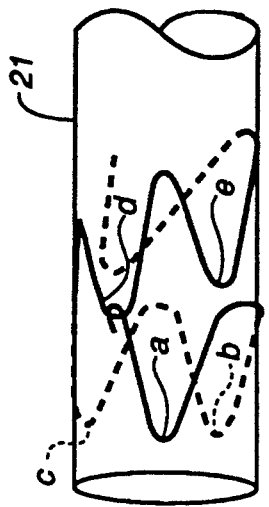
FIG._6

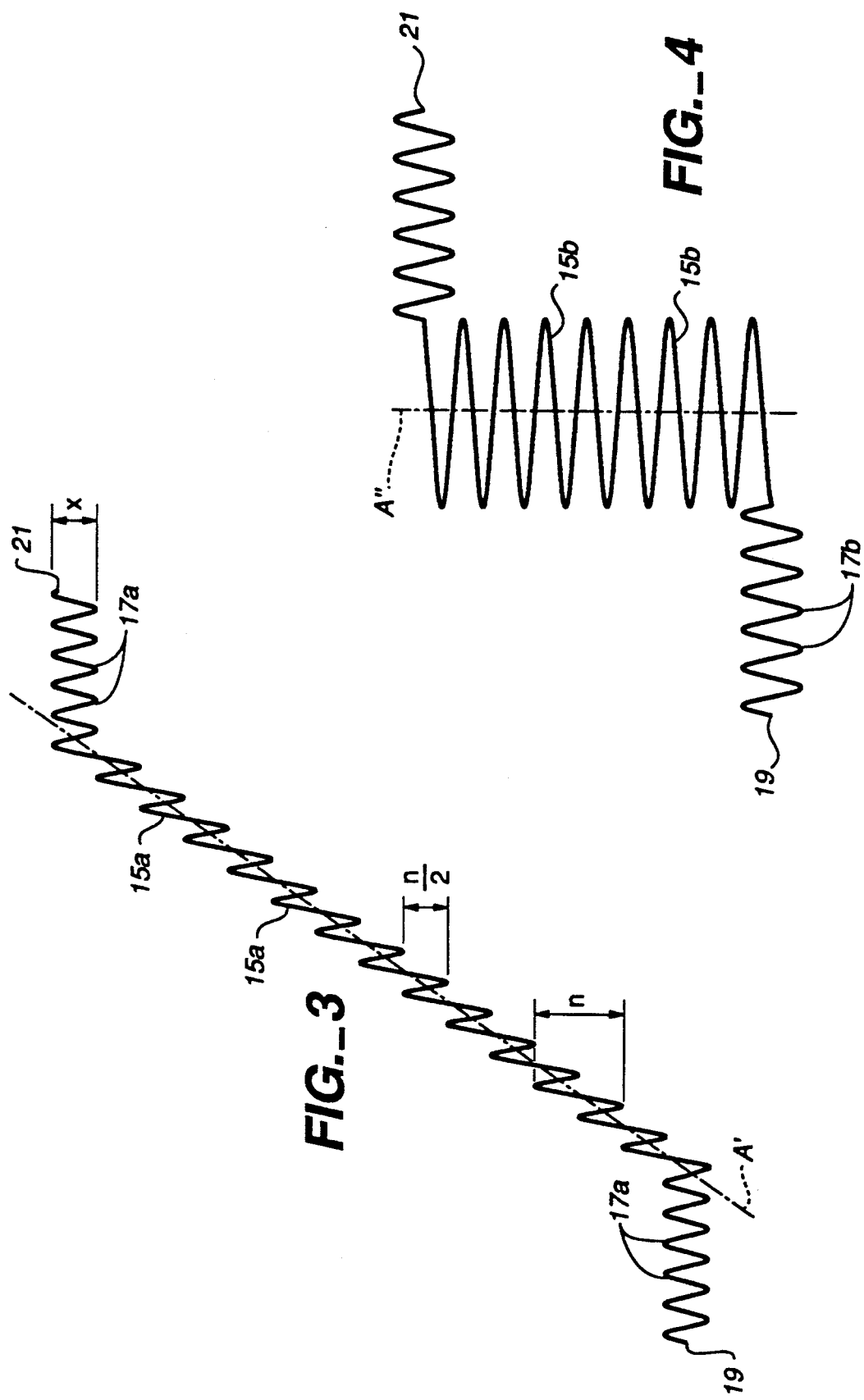

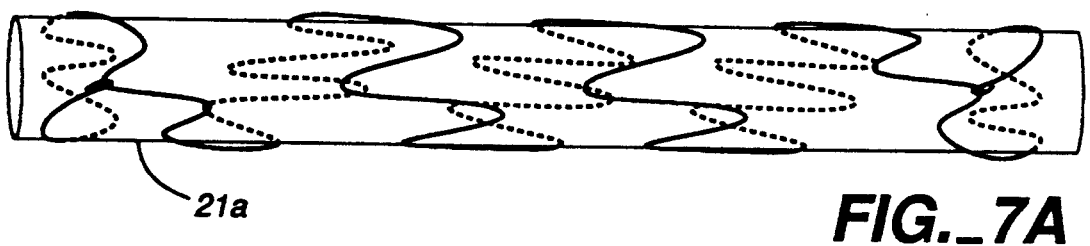
FIG._7A
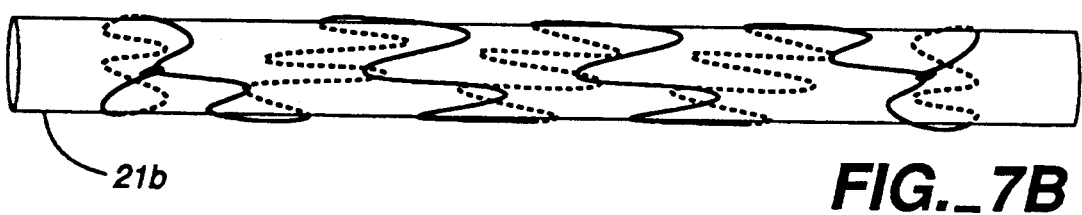
FIG._7B
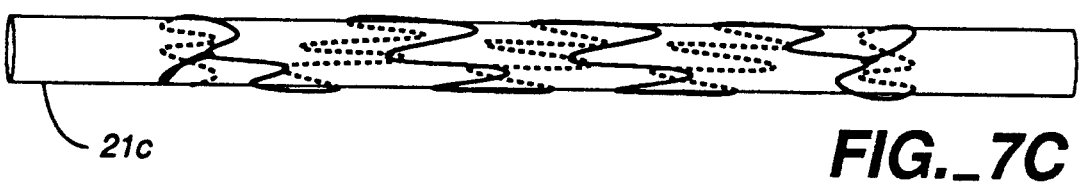
FIG._7C
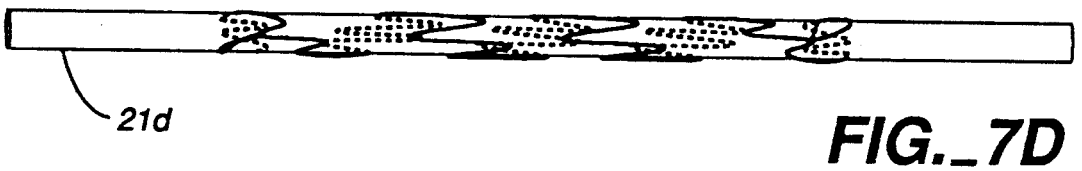
FIG._7D
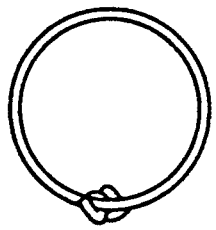
FIG._10
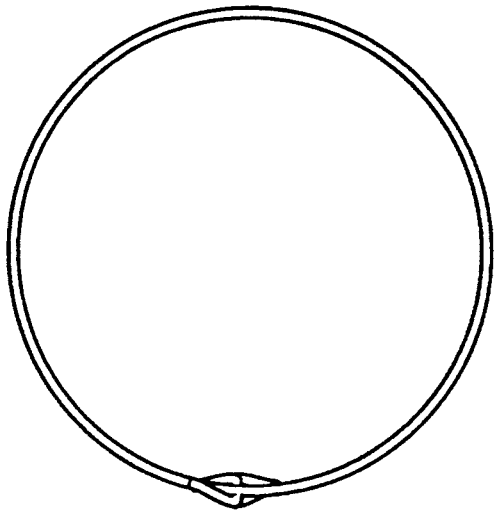
FIG._11

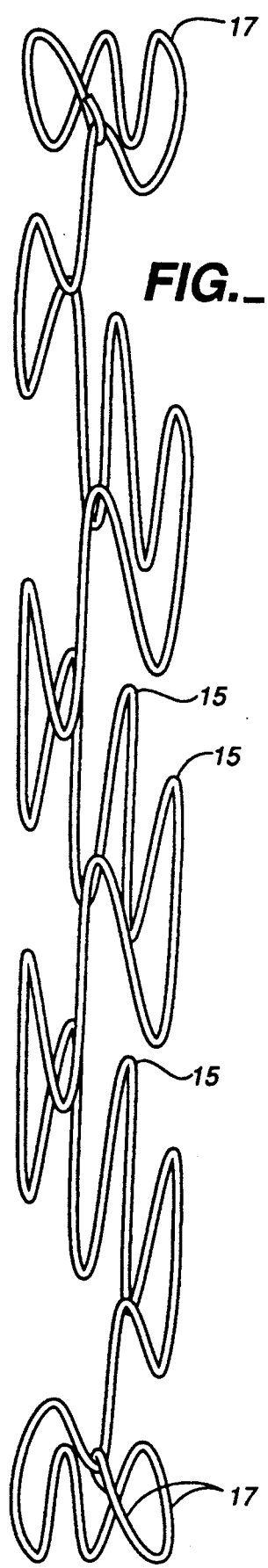
FIG._8
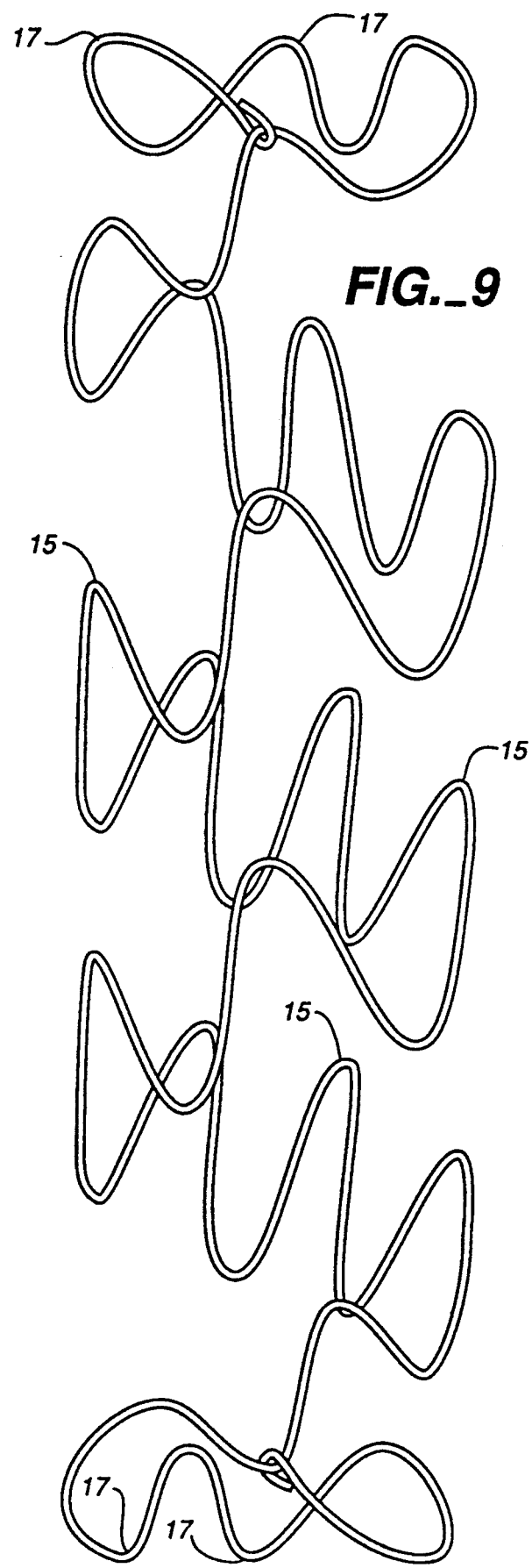
FIG._9

VASCULAR STENT

BACKGROUND OF THE INVENTION

1. Field of the Invention

The present invention generally relates to vascular stents and, more particularly, to vascular stents that each include at least one filament formed into a wave-like pattern.

2. Related Application

The present application is a patent application for copending continuation-in-part applications Ser. Nos. 07/858,304, filed Mar. 25, 1992; 07/874,347, filed Apr. 24, 1992; and 07/943,000, filed Sep. 10, 1992, all of which are commonly assigned herewith. This application is primarily related to copending design application Ser. No. 07/723,525, filed Jun. 28, 1991, and commonly assigned herewith. This application is also secondarily related to copending design applications Ser. Nos. 07/847,247, filed Mar. 9, 1992, and 07/929,150, filed Aug. 13, 1992, both of which are commonly assigned herewith.

3. State of the art

A stent is a device that can be placed within the lumen, or interior space, of a tubular structure to provide support and assure patency of a contracted, but otherwise intact, lumen. (Patency, the state of being freely open, is particularly important in the field of angioplasty, which is concerned with the reconstruction of blood vessels.) A stent can be used, for example, to hold a vessel open or to tack back an intimal flap inside a vessel after angioplasty. More generally, however, a stent can be used inside the lumina of any other conduit including arteries, veins, vessels, the biliary tree, the urinary tract, the alimentary tract, the tracheobronchial tree, the genitourinary system, and the cerebral aqueduct. Furthermore, a stent might be used inside the lumina of an animal other than a human.

The most common angioplastic procedure, percutaneous transluminal coronary angioplasty ("PTCA"), is employed for enlarging narrowed arteries near the heart. In a PTCA procedure, a balloon-tip catheter is introduced into an artery and then expanded, with the effect of dilating a constricted coronary artery. After an arterial lumen is dilated by a stent, the catheter tip is deflated and the catheter is removed from the enlarged artery.

There are several problems associated with conventional PTCA procedures. First, nearly one-third of all PTCA patients suffer from restenosis—a chronic regrowth of the obstructive luminal plaque—that generally occurs within six months of the angioplasty. Because most restenosis patients also display signs of deteriorating cardiac status, they frequently must undergo another PTCA or a coronary artery bypass graft surgery. However, those patients that elect to undergo repeated PTCA procedures tend to restenos at an even higher rate than first-time PTCA patients.

A second, and sometimes fatal, complication of coronary angioplasty is abrupt re-closure, a condition where a dilated vessel completely closes within twenty-four hours after an angioplastic procedure. Several factors may contribute to acute closure. Those contributors include tearing of the wall of the vessel, tissue removal from dissection, spasmodic contractions, and thrombotic formation of blood clots in a vessel.

Although a clear link has not been established between acute closure and restenosis, some studies have suggested that nearly fifty percent of all PTCA patients who restenos also show some degree of vessel recoil, or collapse, soon after the procedure. Other studies have linked restenosis to sub-optimal balloon dilation. In any event, it is probably safe to say that any hemodynamic abnormality created by angioplasty can contribute to the thrombus formation and smooth muscle tissue proliferation that result from many unsuccessful procedures. It is important, therefore, to provide vascular stents that minimize hemodynamic disturbances caused by angioplasty.

DESCRIPTION OF THE RELATED ART

U.S. Pat. No. 4,733,665 to Palmaz discloses an expandable intraluminal graft. According to the patent, intraluminal vascular grafts have included coiled stainless steel springs, helically wound coil springs made from an expandable heat-sensitive material, and expanding stainless steel stents formed of stainless wire in a zigzag pattern. FIG. 1A of the patent shows a prosthesis 70 made of elongate members 75, 76 that are fixedly secured at their intersections and have ends 72 and 73 with pointed extremities. FIG. 2A of the patent shows a stent having a plurality of thin bars 78, 79 which are fixedly secured to one another at their intersections.

U.S. Pat. No. 4,856,516 to Hillstead shows an endovascular stent made from a wire having an approximately sinusoidal-shape. The wire is bent into a sequence of loops that are connected by half-hitch junctions aligned with the circumference of the stent. After implantation of the stent, only the peaks of the sinusoidal wire pattern would rest against the vessel wall.

U.S. Pat. No. 4,922,905 to Strecker discloses a tube dilatation catheter that uses a tube-like knitted structure 30 made from overlapping metal wires or plastic filaments. During radial expansion of the knitted structure, the loops forming the individual meshes are deformed beyond the elastic limits of the filament material.

U.S. Pat. No. 4,886,062 to Wiktor discloses an intravascular, radially-expandable stent. According to the patent, the stent includes a cylindrical, open-ended spiral component made of low memory metal wire that provides radial support inside a blood vessel. As shown in FIG. 1 of the patent, the wire is initially preformed into a two-dimensional zigzag form which is typically sinusoidal. The free ends of the wire are wound into tight loops.

SUMMARY OF THE INVENTION

Generally speaking, the present invention provides a vascular stent that includes at least one filament formed into a wave-like pattern. More particularly, the present invention provides a vascular stent comprising at least one filament formed into a wave-like pattern, and then wound into a substantially spiral shape and means for slidable connection of at least one end of the filament to the filament so as to form a hoop at each end of the spiral. Preferably, the connecting means is a loop wrapped around the filament. The filament can include a material selected from the group consisting of gold, titanium, tantalum, stainless steel, copper, nickel, or plastic.

In one particularly preferred embodiment, a vascular stent according to the present invention comprises a filament of low memory bio-compatible material shaped into a plurality of nearly sinusoidal patterns wherein one nearly sinusoidal pattern on one end of the filament has a longitudinal centerline which is substantially parallel to a longitudinal centerline of another nearly sinusoidal pattern at the other end of the filament, the sinusoidal shaped filament being further formed into a spiral; and hoop means at each end of the spiral, concentric with an centerline of the spiral and formed from the sinusoidal patterns at each end of the filament.

BRIEF DESCRIPTION OF THE DRAWINGS

The present invention can be further understood with reference to the following description in conjunction with the appended drawings, wherein like elements are provided with the same reference numerals. In the drawings:

FIG. 1 shows a filament shaped into a compressed planar wave used to make the nearly sinusoidal waveform of FIG. 2;

FIG. 2 shows the planar wave of FIG. 1 expanded along its longitudinal centerline to form a nearly sinusoidal waveform used in making a stent;

FIG. 3 shows a preferred alternative waveform that can be also be used in making a stent;

FIG. 4 shows another alternative waveform that can be used in making a stent;

FIG. 5 shows the waveform of FIG. 3 spirally wrapped around a round mandril;

FIG. 6 shows a connection for the end of the filament after the preferred waveform is completely wrapped around the mandril;

FIGS. 7(a) through 7(d) show the preferred waveform after it is spirally wrapped on one mandril and is compressed in the radial and longitudinal directions on successively smaller mandrels;

FIG. 8 shows a side view of one embodiment of the stent in its non-expanded form;

FIG. 9 shows a side view of the stent of FIG. 8 after it has been internally expanded;

FIG. 10 is an end view of the stent of FIG. 8; and

FIG. 11 is an end view of the stent of FIG. 9.

DESCRIPTION OF THE PREFERRED EMBODIMENTS

FIG. 1 shows a filament 11 formed in a compressed planar waveform. Preferably, the filament 11 is made from 0.010 inch diameter stainless steel wire; however, it can be made from materials such as titanium, tantalum, gold, copper and copper alloys, combinations of these materials, or any other biologically-compatible material with a low shape-memory level. (In the present context, a low shape-memory level implies that the stent will not contract to its compressed shape after it is inserted and internally expanded in a lumen.) The filament 11 can also be formed from several separate strands which are wrapped or woven together.

The compressed waveform pattern in FIG. 1 is preferably formed generally in the shape of a compressed sinusoid, but can have any wave-like pattern. In the drawing, it should be noted that the waveforms at the ends 19 and 21 of the wire having smaller amplitudes than the waveforms 15 in the middle of the wire. The drawing shows, for example, four reduced amplitude peaks 17 at each of the ends 19 and 21, respectively. Preferably, the heights of the reduced amplitude waveforms 17 are one-half to two-thirds of the heights of the larger waveforms.

In FIG. 2, the compressed waveforms of FIG. 1 are expanded along their longitudinal centerline into a nearly sinusoidal waveform by stretching the compressed waveforms from their ends. (The broken line shows the longitudinal centerline of the expanded waveforms.) At both ends 19 and 21, the longitudinal centerline of the smaller waveforms is displaced from the longitudinal centerline of the waveforms near the middle of the wire. At one end 19, for instance, the centerline of the smaller waveforms 17 is displaced below the broken line; at the end 21, by way of contrast, the centerline of the smaller waveforms is displaced above the broken line.

In practice, the above-described expanded waveforms preferably have a period of about eight millimeters. The larger waveforms 15 preferably have a peak-to-peak amplitude of eight millimeters while the smaller waveforms 17 are one-half to two-thirds the height of the larger waveforms. Although all of the waveforms normally have the same period, they are not necessarily sinusoidal, regular, repeating, or continuous.

FIGS. 3 and 4 show the expanded state of two alternative waveforms that can be used to form a stent according to the present invention. In FIG. 3, the longitudinal centerlines of the small waveforms 17a at the ends of the device are approximately parallel to each other, but the centerline of the large waveforms 15a is inclined relative to the longitudinal centerlines of the smaller waveforms, preferably at an inclination angle of approximately 45°. The inclination of waveforms 15a is the result of this portion of the waveform being made up of substantially straight wire segments of alternating length serially connected by bent wire segments as shown in FIG. 3. In FIG. 4, the waveform is similar to that of FIG. 3 except that the centerline of the larger waveforms 15b is perpendicular to the centerline of the smaller waveforms 17b; in other words, the inclination angle of the larger waveforms is approximately 90°.

In practice, it is preferred to make a stent from the waveform of FIG. 3 because that waveform can be easily wrapped around a mandril and because hoops are easily created at each end of the stent. (The hoops will be described in more detail below.) The remainder of the present specification will refer to the waveform of FIG. 3 unless otherwise noted.

FIG. 5 shows the expanded waveform of FIGS. 3 formed into a stent by wrapping around a mandril 21. Similar waveforms could be used. For instance, if the waveform of FIG. 4 were used, the longitudinal centerline of the large waveforms would remain parallel to the centerline of the mandril and the peaks of the waveforms would be wrapped around the mandril, perpendicular to the centerline of the mandril.

As shown in FIG. 5, the centerline of the large waveforms 15a is arranged to spiral along the length of the mandril 21. One side of each of the larger waveforms 15a is arranged approximately parallel to the longitudinal axis of the mandril 21, and the remaining sections of each of the waveforms is arranged at a small angle to the longitudinal axis of the mandril. (In the drawing, the "small" angle has been greatly exaggerated for purposes of illustration.) It will be appreciated that the illustrated arrangement allows the stent to be wound in a very tight spiral.

By forming the above-described stent as a tight spiral on a mandril, the stent expands primarily in the radial direction, with relatively slight movement at the ends, as it is expanded internally in a lumen. Although even greater radial expansion would be achieved by the wrapping the waveform as a circle around the mandril, such a configuration would cause problems when placed in a lumen because the centerline of the waveform would run around the inside circumference of the lumen and would prevent substantial longitudinal movement of the expanded stent. Also, radially-wrapped configuration would use an excessive amount of filament per unit surface area to support the lumen.

In FIG. 6, each of the last three smaller waveforms 17a at the end of the stent is wrapped with its longitudinal centerline around the circumference of the mandril. It should be noted that the peaks of the last three smaller waveforms (indicated in the drawing by the letters "a", "b" and "c", respectively) are approximately the same distance from the edge of the mandril, and the fourth peak "d" is slightly further away from the end of the mandril. Also, the end of the stent near peak "a" is connected to the apex of peak "d." The result of this connection is that peaks "a", "b", and "c" ar substantially equally spaced around the circumference of the mandril and are all at the approximately same distance from the end of the mandril.

In practice, the connection between the loop and the filament is slidable along the filament 11, thereby allowing for radial expansion. Although this connection can be easily made using a loop as shown, it can also be made by, for example, using a bracket.

FIGS. 7(a) through 7(d) show the waveform of FIG. 3 compressed in the longitudinal and radial directions on successively smaller mandrels. The waveforms can also be twisted as they are compressed. Preferably, the process is started with a 24 french mandrel and is performed in two french increments finishing with an 8 french mandrel. (A french is a unit of measurement equivalent to circumference in millimeters.) In practice, the stent will typically be compressed to about 4.2 centimeters in length. That size of stent can then be inserted into a lumen using a 4 centimeter long, 5 french-diameter angioplasty balloon.

When the above-described stent is wound around a mandril in the shape of a tight spiral, the non-expanded form of the stent provides a profile that is lower than conventional, and the "tines" of the non-expanded stent are generally parallel and packed closely together. This is important because such stent can be accommodated through a smaller incision and, therefore, reduces blood loss during surgery. Furthermore, such a stent can provide an expansion ratio of about 5:1, enabling it to be used in large arteries.

FIG. 8 shows the final form of the above-described stent before it is internally expanded in a lumen, and FIG. 9 shows the stent expanded as by an angioplasty balloon. (The preferred type of angioplasty balloon for inserting the above-described stent is one that is not folded and, therefore, does not have "wings" that prevent the stent from assuming a cylindrical shape when the balloon is expanded.) In these two cases, the outside shape of the stent is round, but the stent can assume other shapes that match the inside wall of a lumen.

As shown in FIGS. 10 and 11, the connections at the ends of the filament 11 create a circular hoop near each end of the stent with no sharp edges, or points, protruding from the perimeter to project into a lumen or to catch on the balloon or plaque inside of a vessel. Also, because the centerline of the smaller waveforms is arranged along the circumference of the stent, the end hoops allow the stent to fit snugly inside the lumen and prevent migration. In other words, in this arrangement, the hoops expand radially to lock the expanded stent in place in a lumen while permitting only limited longitudinal expansion.

Various advantages of the present invention can now be understood. For example, the above-described stent uses substantially less material than conventional stents (especially knitted ones with overlapping wires) and, therefore, introduce a substantially lesser quantity of foreign material into a lumen. As another example, the above-described stent connects its filament ends back onto the filament 11 to prevent thrombosis in blood vessels or damage to any type of a lumen wall such as is caused by stents that have loose wire ends that protrude into a lumen.

Another advantage of the above-described stent is that it provides substantial radial expansion with only limited longitudinal migration and, therefore, reduces the problem of migration inside a lumen. More particularly, the hoops at each end of the above-described stent reduce migration by securing the stent inside of a lumen. In the preferred embodiment, the hoops—as well as the spiral shape of the stent itself—are oriented to inhibit longitudinal growth of the stent during radial expansion.

Yet another advantage of the above-described stent is that it provides sufficient flexibility to allow implantation in tortuous lumens and in applications where lumen bending is required. This overcomes the problem with conventional stents that are so stiff that they are difficult to negotiate through a tortious vessel during implantation. Furthermore, a stiff stent can cause damage to certain vessels, such as those around joints, that require flexibility.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A vascular stent having a longitudinal axis comprising:
   wire bent into a waveform pattern and having a middle portion spirally wrapped into a hollow cylindrical shape;
   said middle portion being made up of successively converted substantially straight wire segments of alternating short and long lengths serially connected by bent wire segments; and
   wherein the longer length of said substantially straight wire segments of alternating short and long lengths is substantially parallel to said longitudinal axis when the stent is in a radially compressed state.

2. A vascular stent having a longitudinal axis comprising:
   wire bent into a waveform pattern and having a portion spirally wrapped into a hollow cylindrical shape;
   said waveform pattern including a plurality of substantially straight wire segments serially connected by bent wire segments, successively connected said straight wire segments alternating between short and long lengths; and a plurality of said straight wire segments being substantially parallel to said longitudinal axis when the stent is in a radially compressed state.

3. The vascular stent of claim 2 wherein about half of said straight wire segments are said long length and about half of said straight wire segments are said short length.

4. The vascular stent of claim 3 wherein said long length straight wire segments are substantially parallel to said longitudinal axis when the stent is in a radially compressed state.

5. A vascular stent having a longitudinal axis comprising:
   wire bent into a waveform pattern and having a portion spirally wrapped into a hollow cylindrical shape; and
   successively connected said waveform pattern including a plurality of substantially straight wire segments serially connected by bent wire segments said successively connected said straight wire segments alternate between long and short lengths.

6. The vascular stent of claim 5 wherein a plurality of said straight wire segments are substantially parallel to said longitudinal axis when the stent is in a radially compressed state.

7. The vascular stent of claim 6 wherein said long length straight wire segments are substantially parallel to said longitudinal axis when the stent is in a radially compressed state.

8. A vascular stent comprising:
   a longitudinal axis;
   a filament formed into a wave-like pattern having a middle portion and a first end portion, said middle portion being wrapped into a radially expandable shape around said longitudinal axis and having a longitudinal centerline, said middle portion also including a plurality of substantially straight wire segments serially connected by bent wire segments, successively connected said straight wire segments alternating between short and long lengths, said first end portion extending from aid middle portion and having an amplitude smaller than any amplitude in said middle portion and a longitudinal centerline inclined to said longitudinal centerline of said middle portion; and
   a hoop formed around said longitudinal axis and from said first end portion.

9. The vascular stent of claim 8 wherein said wave-like pattern further has a second end portion extending from said middle portion and wherein said stent further comprises another hoop formed around said longitudinal axis and from said second end portion.

10. The vascular stent of claim 9 wherein said second end portion has a longitudinal centerline parallel to said longitudinal centerline of said first end portion.

11. The vascular stent of claim 9 wherein said second end portion has a longitudinal centerline inclined to said longitudinal centerline of said middle portion.

12. The vascular stent of claim 9 wherein said second end portion has an amplitude smaller than said any amplitude in said middle portion.

13. The vascular stent of claim 8 wherein said wave-like pattern comprises a planar waveform.

14. The vascular stent of claim 8 further comprising means for slidably connecting one end of said filament to said filament and forming said hoop.

15. The vascular stent of claim 8 wherein said means for slidably connecting is a loop at said one end of said filament.

16. The vascular stent of claim 8 wherein said longitudinal centerline of said first end portion is displaced from said longitudinal centerline of said middle portion.

17. The vascular stent of claim 8 wherein said longitudinal center of said first end portion is substantially perpendicular to said longitudinal centerline of said main portion.

18. The vascular stent of claim 8 wherein said radially expandable shape of said middle portion of said filament is a substantially spiral shape.

19. The vascular stent of claim 8 wherein said longitudinal centerline of said first end portion is positioned along an outermost circumference of said stent.

20. The vascular stent of claim 8 wherein a group of said successively connected said straight wire segments alternating between said long and short lengths is substantially parallel to said longitudinal axis of said stent.

* * * * *